United States Patent [19]

Wang

[11] Patent Number: 5,610,272
[45] Date of Patent: Mar. 11, 1997

[54] SOLID PHASE PROCESS FOR SYNTHESIZING THYMOSIN $\alpha_1$

[75] Inventor: Su S. Wang, Belmont, Calif.

[73] Assignee: Alpha-1 Biomedicals, Inc., Bethesda, Md.

[21] Appl. No.: 684,520

[22] Filed: Apr. 15, 1991

Related U.S. Application Data

[63] Continuation of Ser. No. 192,349, May 10, 1988, abandoned.

[51] Int. Cl.$^6$ .............................. C07K 1/06; C07K 14/66
[52] U.S. Cl. ...................... 530/334; 530/301; 530/324
[58] Field of Search ..................................... 530/301, 334, 530/324

[56] References Cited

U.S. PATENT DOCUMENTS

| | | |
|---|---|---|
| 4,148,788 | 4/1979 | Wang . |
| 4,207,311 | 6/1980 | Brown et al. . |
| 4,229,438 | 10/1980 | Fujino et al. . |
| 4,244,946 | 1/1981 | Rivier et al. . |
| 4,361,673 | 11/1982 | McGregor .............................. 530/331 |
| 4,382,922 | 5/1983 | Rivier et al. . |
| 4,406,832 | 9/1983 | Mills . |
| 4,507,230 | 3/1985 | Tam et al. . |
| 4,855,407 | 8/1989 | Wang ...................................... 530/324 |

FOREIGN PATENT DOCUMENTS 0200404  11/1986  European Pat. Off. .

OTHER PUBLICATIONS

The Peptides, Analysis, Synthesis, Biology, vol. 2, Gross, pp. 101–108 (1980).
The Peptides, Analysis, Synthesis, Biology, vol. 3, Gross, pp. 15–19, 31–33 (1981).
Wang et al., Chem. Abstr. vol. 109, No. 55211u (1988).
The Peptides, Analysis, Synthesis, Biology, vol. 3, Gross, Academic Press, New York pp. 17 and 212–215, (1981).
Walter, et al., (Ann Arbor Science), "Peptides: Chemistry, Structure and Biology," Jun. 1–6, 1975, pp. 332–339, New York, New York.
Fauchere, et al., "Differential Protection and Selective Deprotection in Peptide Synthesis," The Peptides, 1981, vol. 3, Chapter 5, pp. 203–253.

*Primary Examiner*—Christina Y. Chan
*Attorney, Agent, or Firm*—Sherman & Shalloway

[57] ABSTRACT

4-methyloxybenzyloxycarbonyl (Moz) is used to protect the alpha amino groups of the amino acids used in solid-phase synthesis of thymosin $\alpha_1$. It was found that the Moz group can be removed rapidly and completely with 5–10% trifluoroacetic acid in $CH_2Cl_2$. Some advantages of utilizing Moz-amino acids over Boc-amino acids in solid-phase peptide synthesis are higher yields and purities with reduced consumption of trifluoroacetic acid during the acidolytic cleavage of the $N^\alpha$-Moz groups. Further improvements with respect to the recovery and recycling of the used solvent are obtained by using tributylamine in place of triethylamine as the neutralization agent making it possible to distill methylene chloride from the liquid waste without contamination by the lower boiling triethylamine. Methylbenzhydrylamine resin is the preferred resin support. Cleavage from the resin support and deprotection of the protected side groups of the protected thymosin $\alpha_1$ can be accomplished using either HBr or trifluoromethane sulfonic acid in trifluoroacetic acid with anisole and thioanisole as scavengers.

1 Claim, 5 Drawing Sheets

FIG. 5a
FIG. 5b
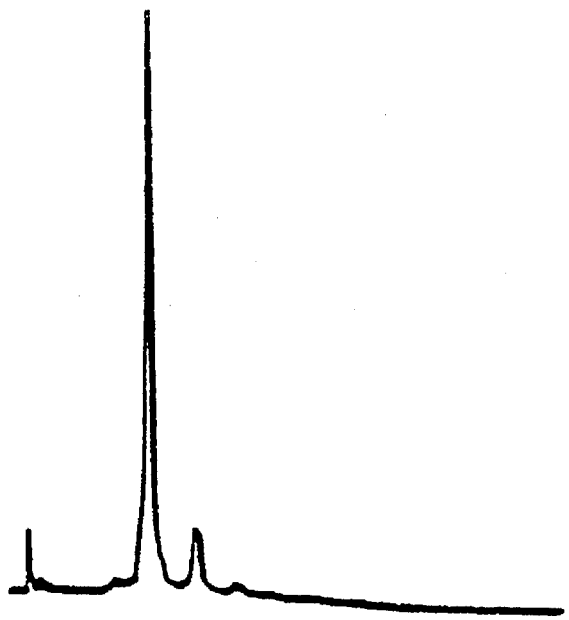
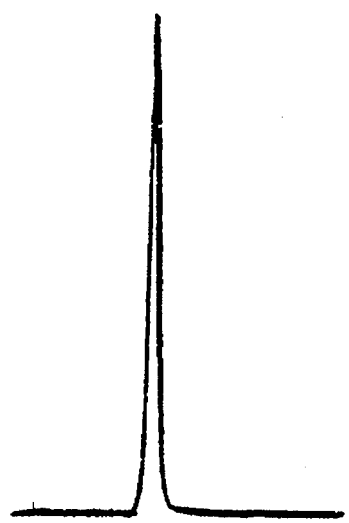

SOLID PHASE PROCESS FOR SYNTHESIZING THYMOSIN $\alpha_1$

This application is a continuation of the application Ser. No. 07/192,349, filed May 10, 1988, now abandoned.

BACKGROUND OF THE INVENTION

Field of the Invention

This invention relates to a process for producing thymosin $\alpha_1$. More particularly, this invention is directed to a solid-phase synthesis for thymosin $\alpha_1$ wherein the alpha amino acid of each successive amino acid is protected by 4-methoxybenzyloxycarbonyl (Moz) protective group followed by acidolytic catalyzed cleavage.

Biologically active peptides generally exhibit their biological activity at very minute dosages, for example, at nanogram levels or lower. Therefore, during the initial screening and testing phases it is generally sufficient to produce the peptide of interest in correspondingly small amounts, such as from a few milligrams to a few grams. In such cases, the volume of liquid reagents required during the synthesis and purification steps as solvents, reactants, diluents, washing agents and the like, while often considerable, for example, from several to tens of gallons, nevertheless, may still be manageable in terms of cost, storage space, disposal and the like. However, for large scale production, for example, in lot sizes of from tens of grams or more, for example, from about 100 grams to 2 kilograms, especially 250 grams to 1 kilogram (on dry basis) the problems of product recovery, product purity, and reagent handling, storage and disposal have presented such difficulties that there are virtually no satisfactory large scale processes available. As a result there is a great need in the art for a solid-phase peptide synthesis process capable of producing peptide materials of commercial interest, whether for large scale clinical trials or for other commercial applications, in large batch quantities.

This need is even more urgent for relatively long peptides, i.e., of from about 10 or more amino acids in the peptide, especially from about 15 to 50 amino acid sequences. For example, even using an automated solid-phase peptide synthesizer machine, each full cycle of protection of functional groups, coupling, cleavage of peptide from resin, purification and so on will take from one day to several days or weeks, with the total production process requiring as long as up to 6 to 8 months in some cases. Since this time period is largely independent of batch size it can be readily appreciated that, on a unit basis, production costs are extremely high, when only small gram quantities are produced.

In U.S. Pat. No. 4,079,127, thymosin $\alpha_1$ is shown to have a molecular weight of 3,108 and a pI' in the range of 4.0–4.3 as determined by slab gel isoelectric focusing at a pH range of 3–5. The compound has the following amino acid sequence:

Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH.

Thymosin $\alpha_1$ has been found to be 10 to 1,000 times more active than thymosin fraction 5 in several in vitro and in vivo assay systems designed to measure T-cell differentiation and function. Thymosin $\alpha_1$ may be administered to warm blooded mammals by parenteral application either intravenously, subcutaneously or intramuscularly. The compound is a potent immunopotentiating agent with a daily dosage in the range of about 1 to 100 μg/kg of body weight per day for intravenous administration. Obviously, the required dosage will vary with the particular condition being treated, the severity of the condition and the duration of the treatment.

In U.S. Pat. No. 4,148,788, the present inventor described the synthesis of thymosin $\alpha_1$ by solid-phase peptide synthesis and by fragmentation condensation. These processes both used tert. butyloxycarbonyl (Boc) as the protecting group for the α-amino acid during the coupling reactions of the C-terminal amino acid to the solid support resin and for the coupling of each successive amino acid.

The Boc group has been the preferred amino protecting group for solid-phase peptide synthesis in view of its stability to the condensation (coupling) conditions, its ease of removability without destruction of the peptide bonds or racemization of chiral centers in the peptide chain, and its low cost. This preference for the Boc protective group is clearly manifested in the patent and general literature by the almost exclusive use of Boc as the protective group for protecting alpha-amino acids.

For instance, G. Barany and R. B. Merrifield in *The Peptides, Analysis, Synthesis, Biology*, Vol. 2, "Special Methods in Peptide Synthesis", Part A. Ed. By E. Gross and J. Meienhofer, Academic Press, Inc., New York, 1980, state in Chapter 1, Solid-Phase Peptide Synthesis at pages 101–102, that "[t]he tert-butyloxycarbonyl (Boc) group . . . is by far the most widely used functionality for α-amino protection in solid-phase peptide synthesis." Other tert-alkyl urethane forming α-amino protecting groups mentioned by the authors include tert-amyloxycarbonyl (Aoc), adamantyloxycarbonyl (Adoc), and 1-methylcyclobutyloxycarbonyl (Mcb). This text also describes 10 different combinations of inorganic (protic or Lewis) and organic (including carboxylic) acids, in solvent (usually anhydrous) mixtures. Among these combinations are neat anhydrous trifluoroacetic acid (TFA) and TFA-$CH_2Cl_2$ in ratios (v/v) from 1:4 to 1:1, 25° C., 20–30 minutes.

Under the heading "3. Other Amino-Protecting Groups Removable by Acidolysis" pages 106–107, Barany and Merrifield report that the benzyloxycarbonyl (Z) group, which is removed by strong acids such as HBr in acetic acid, was the first group examined for solid-phase synthesis, but that "[g]iven the overall status of current methodology, $N^\alpha$-protection with the benzyloxy group will probably be restricted to the $NH_2$-terminal residue of a peptide. The widely applied protection scheme for solution synthesis, relying on the hydrogenolyzable $N^\alpha$-benzyloxycarbonyl group and acidolyzable side-chain tert-butyl derivatives . . . has not been applicable for solid-phase synthesis."

On the other hand, the authors also report on work by others using furfuryloxycarbonyl (Foc) and p-methoxybenzyloxycarbonyl (Moz) groups. They state at page 107 that these "groups are primary urethanes that are deprotected under the same acidolytic conditions and at essentially the same rates as the tert-butyloxycarbonyl groups . . . Hence, they have occasionally been used in stepwise solid-phase synthesis. The ultraviolet absorbing chromophore of [Moz] facilitates spectrophotometric monitoring of deprotection and coupling steps."

In the aforementioned U.S. Pat. No. 4,148,788 only Boc is disclosed as the α-amino protecting group although as the protecting group for the ω-amino group of lysine (Lys) the benzyloxycarbonyl (Z) protecting group is used and other ω-amino protecting groups are disclosed, including benzyloxycarbonyl substituted in the aromatic ring, such as by 4-chloro, 2-bromo, 4-bromo, 2,4-dichloro, 4-nitro, 4-methoxy, 3,5-dimethoxy, 4-methyl, 2,4,6-trimethyl, 4-phenylazo, 4-(4-methoxyphenylazo), 2-(N,N-dimethylcarbonamido), 4-dihydroxyboryl, and 2-nitro-4,5-dimethoxy, urethane type protecting groups, such as 4-toluenesulfonylethyloxycarbonyl, 9-fluorenylmethoxycarbonyl (Fmoc) and related base cleavable groups, 5-benzisoxazolylmethyleneoxycarbonyl, methylthio- and methylsulfonylethyloxycarbonyl, isonicotinyloxycarbonyl, haloethyloxycarbonyl, diisopropylmethyloxycarbonyl, benzhydryloxycarbonyl, isobornyloxycarbonyl, dinitrodiphenylmethyloxycarbonyl, tert. butyloxycarbonyl, tert. amyloxycarbonyl, adamantyloxycarbonyl, cyclopentyloxycarbonyl, and others; acyl groups, such as formyl, trifluoroacetyl, phthaloyl, benzenesulfonyl, and others; and aryl-lower alkyl groups, such as diphenylmethyl and triphenylmethyl.

In the recently published European Patent Application 0 200 404 published Nov. 5, 1986, and corresponding to U.S. application Ser. No. 722,218, filed Nov. 4, 1985, now abandoned, and to continuation-in-part application Ser. No. 849,835, filed Apr. 9, 1986, now U.S. Pat. No. 4,855,407, issued Aug. 8, 1989, the present applicant disclosed an improved solid-phase peptide synthesis of thymosin $\alpha_1$, using methylbenzhydrylamine (MBHA) resin as the solid support and hydrogen bromide (HBr) with trifluoroacetic acid (TFA) and anisole and thioanisole as the cleavage and deprotection agents. Here too, Boc is disclosed as the preferred, and is used as the, alpha-amino protecting group. Other $\alpha$-amino protecting groups are mentioned, including benzyloxycarbonyl (Z), biphenylisopropyloxycarbonyl, t-amyloxycarbonyl, isobornyloxycarbonyl, 1,1-dimethyl-3,5-dimethyloxybenzyloxycarbonyl (Ddz), o-nitrophenylsulfenyl, 2-cyano-t-butyloxycarbonyl and 9-fluorenylmethyloxycarbonyl.

The patent literature, disclosing solid-phase peptide synthesis of peptides, other than thymosin $\alpha_1$, also substantially exclusively exemplifies Boc as the alpha,amino protecting group, notwithstanding general disclosures of other protecting groups, such as benzyloxycarbonyl (Z) and substituted Z groups, including, for example, those mentioned above as protecting group for $\omega$-amino functional groups.

On the other hand, for classical liquid phase (solution) peptide synthesis reactions, the benzyloxycarbonyl (Z) and Boc alpha-amino protecting groups are used with about equal frequency. Thus, while acidolytic cleavage of alpha-amino protecting groups has been the subject of considerable research, the general conclusion in the art has been that the acid sensitivities of the Boc or 4-methoxy substituted Z, i.e. 4-methoxybenzyloxycarbonyl (Moz), protecting groups are roughly equal. So far as the applicant is aware, however, no precise or rigorous comparison has ever actually been conducted to test the relative acid sensitivities of Boc and Moz in solid-phase peptide synthesis.

In the aforementioned U.S. application Ser. Nos. 722,218 and 849,835, U.S. Pat. No. 4,855,407 and the corresponding published application 0,200,404 the advantages of using hydrogen bromide as the acid cleavage and deprotection agent in place of the more highly corrosive hydrogen fluoride were described.

However, the use of HBr does present the drawback that, being a gas, it is brought into contact with the resin-bound protected thymosin $\alpha_1$ by bubbling the gaseous HBr into a solution of the resin-bound protected peptide in, usually, trifluoroacetic acid. The bubbling procedure is not only slow but also requires pressurized gas tanks and still requires some degree of skill in its use. Therefore, it would be desirable to find a liquid acid cleavage agent which does not present the corrosion problems inherent to HF and can be used with ordinary laboratory glassware or plastic yet is at least as highly efficient and selective in the acid cleavage and deprotection of the resin-bound protected thymosin $\alpha_1$ peptide.

Accordingly, it is an object of this invention to provide an improved solid-phase synthesis of thymosin $\alpha_1$ in high yield and high purity.

Another object of the invention is to provide an improved solid-phase synthesis of thymosin $\alpha_1$ which can be easily and efficiently carried out without requiring highly skilled technicians and which avoids the use of gaseous reactants for the cleavage and deprotection of the resin-bound protected thymosin $\alpha_1$ peptide.

It is another object to provide a solid-phase synthesis for thymosin $\alpha_1$ which is capable of large scale synthesis using standard equipment and apparatus.

These and other objects of the invention which will become more apparent upon review of the following detailed description and preferred embodiments, including the accompanying drawing figures, are provided by the solid-phase peptide synthesis for production of thymosin $\alpha_1$ in which during synthesis the nitrogen of the alpha-amino group ($N^\alpha$) of each amino acid is bonded to 4-methoxybenzyloxycarbonyl (Moz) and cleavage is carried out using greatly reduced quantity of trifluoroacetic acid (TFA).

According to another aspect of the invention, in a preferred embodiment thereof, the step of cleavage and deprotection of the resin-bound protected thymosin $\alpha_1$ peptide is carried out using trifluoromethane sulfonic acid (TFMSA), by adding the TFMSA, preferably together with anisole and thioanisole, to a suspension of the resin-bound protected peptide in, preferably, trifluoroacetic acid.

In accordance with this invention, thymosin $\alpha_1$ or a biologically active analog or fragment thereof is prepared by solid-phase peptide synthesis by the steps of (a) temporarily chemically protecting the reactive amino group at the alpha-position and any other reactive groups, other than the carboxylic acid group at the beta-position, on the C-terminal amino acid of the thymosin $\alpha_1$ peptide;

(b) chemically bonding the protected C-terminal amino acid via the carboxylic acid (—COOH) group thereof to a resin support;

(c) chemically deprotecting the reactive amino group of the resin-bound protected amino acid by acidolytic cleavage using dilute trifluoroacetic acid solution;

(d) chemically coupling via a peptide bond the next amino acid in the desired sequence by contacting the resin-bound amino acid from step (c) with said next amino acid having all of the reactive groups thereof, other than the carboxylic acid group at the alpha-position, chemically protected, in the presence of a coupling agent;

(e) chemically deprotecting the reactive amino group of the coupled amino acid from step (d) by acidolytic cleavage using dilute trifluoroacetic acid solution;

(f) continuing the synthesis by repeating steps (d) and (e) with successive amino acids in the desired sequence being added one at a time until the total desired sequence of the protected peptide is built up on the resin, and (g) cleaving the protected peptide from the resin support and deprotecting the protected side-chain reactive groups;

wherein the volume of trifluoroacetic acid solvent is substantially reduced by temporarily chemically protecting the alpha-amino acid in step (a) and in step (D) with 4-methoxybenzyloxycarbonyl.

Preferably, the resin support in step (b) is methylbenzhydrylamine resin and step (g) is carried out with hydrogen bromide or trifluoromethane sulfonic acid.

DETAILED DESCRIPTION OF THE INVENTION

Figure 1:
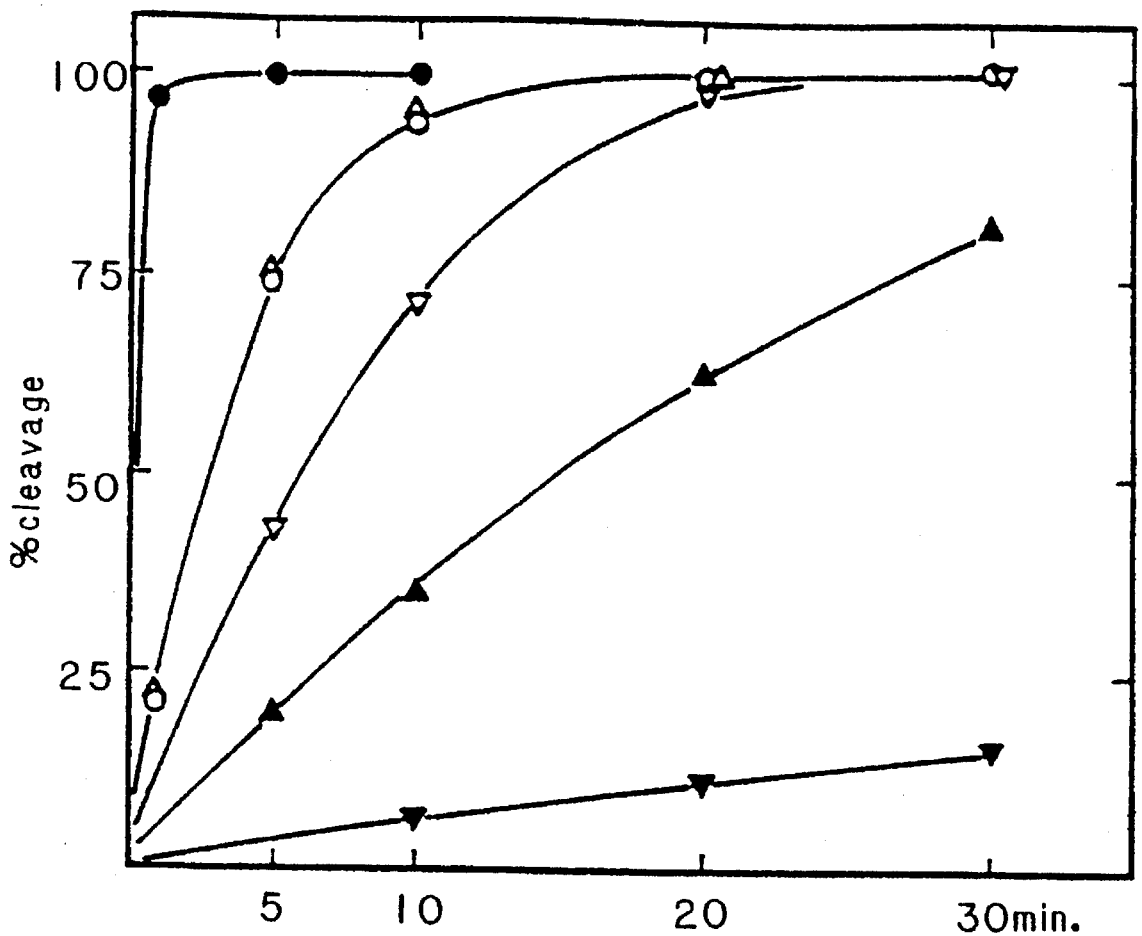
FIG. 1 is a graphic representation of acid cleavage rates of Moz-Ala-Leu-Leu-Leu-Leu-Leu-Val-OCH$_2$-C$_6$H$_4$-Resin by 10% TFA (●—●) and by 5% TFA (○—○) and Boc-Ala-Leu-Leu-Leu-Leu-Leu-Val-OCH$_2$-C$_6$H$_4$-Resin by 40% TFA (∆—∆), 20% TFA (∇—∇), 10% TFA (▲—▲) and 5% TFA (▼—▼)

The present inventor has now discovered, and this forms the essence of the present invention, that the Moz-amino acid is significantly more sensitive to acid cleavage (deprotection) than the corresponding Boc-amino acid in solid-phase peptide synthesis. This greater sensitivity is manifested, in actual practice, by much higher rates of deprotection requiring much lower quantities of acidic deprotecting agent.

The greater lability of the Moz-group to acid deprotection means that the selectivity between the N$^\alpha$ protecting group and the benzyl-based protecting groups on the side chain or anchoring bonds to the resin is much greater. Therefore, losses of peptide chains from the support will be reduced and side reactions due to premature side chain deprotection will be minimized. Furthermore, deletion peptides resulting from incomplete removal of the N$^\alpha$ group can be avoided more easily. Another advantage of the Moz-group lies in the ability to monitor coupling and deprotection reactions spectroscopically. Still another advantage of using Moz-amino acids instead of Boc-amino acids in solid-phase peptide synthesis resides in the considerable cost saving that can be made since much less TFA is needed, especially in large scale preparation of biologically active peptides. Furthermore, unlike other acid sensitive amino protecting groups, such as 2-(p-biphenyl)propyl-2-oxycarbonyl (Bpoc), α,α-dimethyl-3,5-dimethyloxybenzyloxy carbonyl (Ddz), etc., that are expensive to make, the costs for preparing Moz-amino acid derivatives are about the same as those for Boc-amino acids.

To illustrate the usefulness of Moz-amino acids, the automated synthesis of the model tetrapeptide Leu-Ala-Gly-Val (LAGV) was undertaken. For the synthesis, the details of which are shown in Referential Example 2 below, 30 minutes treatment in 10% TFA was utilized to deprotect the Moz-group in each synthetic cycle. As control experiments, parallel synthesis of the same peptides was performed under the exactly identical conditions with Boc-amino acids as synthetic materials and 40% TFA in CH$_2$Cl$_2$ (30 minutes) as deprotecting agent.

Thus, Moz-Val-OCH$_2$-C$_6$H$_4$-Resin prepared from ClCH$_2$-C$_6$H$_4$-Resin and Moz-Val-OH via the cesium salt method as disclosed, for example, by Gisin, B. F., *Helv Chim, Acta.*, 56, 1476–1482 (1973) and in *Solid-Phase Peptide Synthesis*, 2nd Ed. by J. M. Stewart and J. D. Young, Pierce Chemical Co., Rockford, Ill. (1984), the disclosures of which are incorporated herein by reference thereto, was used as the starting material for the automated synthesis of Moz-Leu-Ala-Gly-Val-OCH$_2$-C$_6$H$_4$-Resin. After HF-cleavage of this tetrapeptide resin, a sample of crude LAGV was obtained. Amino acid analysis and HPLC analysis showed that the material was about 98% pure. It was then subjected to an ion-exchange chromatographic analysis on an amino acid analyzer according to the procedure described by R. B. Merrifield, et al. *J. Org. Chem*, 39, 660–668 (1974), the disclosure of which is incorporated herein by reference thereto. The results were compared with those derived from a corresponding crude LAGV sample obtained from a parallel synthesis using Boc-amino acids. The results are tabulated in Table I. The levels of deletion-peptides present in the Moz-sample were found to be generally lower than those present in the Boc-sample.

TABLE 1

| | Crude Leu—Ala—Gly—Val (LAGV) prepared from Moz-amino acids or Boc-amino acids.[a] | | | | |
|---|---|---|---|---|---|
| LAGV Sample[b] | LAGV (%) | AGV (%) | LAV (%) | LGV (%) | AV + GV (%) |
| From Moz-method | 98.8 | 0.32 | 0.27 | 0.32 | 0.28 |
| From Boc-Method | 97.9 | 0.43 | 0.40 | 0.31 | 0.97 |

[a]To enhance the differences, single couplings were used for this comparison. Deletion peptides are greatly reduced by double coupling protocols. The numbers given are the average of two analyses.
[b]Crude samples from HF cleavage of the peptide resin were directly injected into the amino acid analyzer BECKMAN 120B where the peptides are well separated. The proportions of the desired tetrapeptide LAGV and the deletion peptides present in the samples are tabulated.

As a further indication of the different relative sensitivities of the Moz- and Boc-amino protecting groups on larger peptides two otherwise identical heptapeptides: Moz-Ala-Leu-Leu-Leu-Leu-Leu-Val-OCH$_2$-C$_6$H$_4$-Resin and Boc-Ala-Leu-Leu-Leu-Leu-Leu-Val-OCH$_2$-C$_6$H$_4$-Resin were prepared and were separately treated with different concentrations of TFA in CH$_2$Cl$_2$. At various time intervals, small samples were withdrawn and immediately quenched with dilute triethylamine (Et$_3$N) in CH$_2$Cl$_2$ followed by thorough washing with CH$_2$Cl$_2$. The neutralized samples were then allowed to couple with Boc-Phe-OH in the presence of N,N'-dicyclohexylcarbodiimide (DCC) until negative to the ninhydrin test. Amino acid analyses were done for each sample and the increase in the ratio of Phe/Ala was taken as the rate of the acidolytic cleavage of Moz- or Boc-group on the heptapeptide-resins. The details of the cleavage reactions are shown in Referential Example 3 below. The results are summarized in FIG. 1. As can be seen, deprotection of the Moz-group proceeded rapidly and completely, requiring much less TFA than deprotection of the Boc-group. The time course for Moz cleavage in 5% TFA coincides almost completely with that for Boc cleavage at 40% TFA. At 10% TFA, Moz was observed to be removed nearly instantaneously with a half-life time of less than 0.3 minutes.

When similar experiments were performed on Moz-Ile-Ala-Leu-Leu-Leu-Leu-Leu-Val-OCH$_2$-C$_6$H$_4$-Resin and Boc-Ile-Ala-Leu-Leu-Leu-Leu-Leu-Val-OCH$_2$-C$_6$H$_4$-Resin to determine whether the rate of acidolysis for Ile would be different from that for Ala, the results indicated that the corresponding rates were identical. No differences were observed when the protecting groups were cleaved from either Ile-peptide-resin or Ala-peptide-resin.

Based on these studies the inventor undertook the solid-phase peptide synthesis of thymosin α$_1$ using the procedures as previously generally described in the aforementioned applications Ser. Nos. 849,835 and 722,218, or in the aforementioned U.S. Pat. No. 4,148,788, the disclosures of which are incorporated herein by reference thereto, but using 4-methoxybenzyloxycarbonyl (Moz) of the formula:

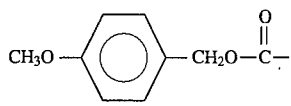

the alpha-amino protecting group in place of tert-butyloxy-carbonyl (Boc) of the formula

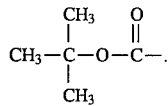

As compared to the synthesis reaction using N$^\alpha$-Boc-amino acid, the reaction using N$^\alpha$-Moz-amino acid produced less impurities and deletion peptides and required substantially less trifluoroacetic acid (TFA) as the acid solvent.

According to the present invention, thymosin α$_1$ having the following sequence Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH, or biologically active position analogs, or fragments, thereof, are produced by solid-phase peptide synthesis using conventional techniques, except that as the N$^\alpha$-amino protecting group, 4-methoxybenzyloxycarbonyl (Moz) is used, and substantially lower volumes of trifluoroacetic acid as the acidic cleavage solvent are required.

The Moz-amino acid preparation can be carried out similarly to the Boc-amino acid preparation as already described in the literature, for example, on pages 31–32 of *The Peptides, Analysis, Synthesis, Biology*, Vol. 3, "Protection of Functional Groups in Peptide Synthesis", Ed E. Gross and J. Meienhofer, Academic Press, New York, 1981, the disclosure of which is incorporated herein by reference thereto.

Each of the steps in the solid-phase peptide synthesis of thymosin α$_1$, according to this invention, will now be described.

Step (a). Protection of the alpha-amino acid

The C-terminal amino acid of thymosin α$_1$ is asparagine (Asn),

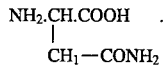

Asn is bonded to the resin support, as aspartic acid (Asp), an amide bond formed between the betacarboxylic acid and the resin support. Therefore, each of the amino group and carboxyl group on the alpha-carbon atoms are chemically protected.

According to the present invention, 4-(or p-)methyloxybenzyloxycarbonyl (Moz) of formula

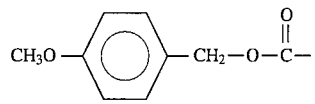

used to protect the N$^\alpha$ group.

The α-carboxylic acid group may be protected by any of the carboxylic acid protecting groups, but preferably with a simple benzyl ester. Thus, the protected C-terminal amino acid to be bonded to the resin support is preferably N$^\alpha$-Moz-α-benzyl-L-aspartic acid.

Step (b). Bonding protected C-terminal amino acid to resin support

As described in the above-mentioned copending application Ser. No. 849,835, filed Apr. 9, 1986, the preferred resin support is methylbenzhydrylamine resin, however, the benzhydrylamine resin can also be used.

The methylbenzhydrylamine resin may be prepared from commercially available polystyrene resin beads (1% divinyl benzene, 200–400 mesh U.S. standard) by reacting the same with p-toluoyl chloride in the presence of a Lewis acid such as aluminum chloride in an inert solvent such as dichloroethane at a low temperature, preferably 0 to 5° C. to form a p-toluoyl resin, CH$_3$—C$_6$H$_4$—CO—C$_6$H$_4$-resin. This resin is reacted with a mixture of ammonium formate, formamide and formic acid at reflux temperature (160°–170° C.) for 24 hours to yield N-formyl methylbenzhydrylamine resin, CH$_3$—C$_6$—H$_4$—CH(NH—CO—H)—C$_6$H$_4$-resin. Upon hydrolysis in dilute hydrochloric acid, the desired methylbenzhydrylamine resin, i.e. CH$_3$—C$_6$H$_4$—CH(NH$_2$.HCl)C$_6$H$_4$-resin, is formed.

The methylbenzhydrylamine resin so formed is neutralized and acylated with N$^\alpha$-Moz-α-benzyl-L-aspartic acid formed in step (a) in the presence of dicyclohexylcarbodiimide to give Moz-asparaginyl resin More specifically, the N$^\alpha$-Moz-α-benzyl aspartic acid protected C-terminal amino acid is attached to the methylbenzhydrylamine resin by means of an N,N'-dicyclohexylcarbodiimide (DDC)/1-hydroxybenzotriazole (HBT) mediated coupling for from about 2 to 24 hours, preferably about 12 hours at a temperature of between about 10° and 50° C., preferably 25° C., in a solvent such as dichloromethane or dimethylformamide (DMF), preferably dichloromethane.

Step (c). Chemical deprotection

Chemical deprotection of N$^\alpha$-Moz group is accomplished by acidolysis using trifluoroacetic acid (TFA). However, unlike conventional deprotection schemes using anhydrous TFA or TFA: CH$_2$Cl$_2$ mixtures at (v/v) of 1:4 to 1:1 the TFA concentration in CH$_2$Cl$_2$ can be greatly reduced, such as 1:5 to 1:50, preferably 1:5 to 1:20. Usually, TFA will be used at about a 10% v/v concentration, such as from 8 to 15%. At these low TFA concentrations the benzyl ester protecting group is much more resistant to acidolytic cleavage and, as a result, fewer unwanted by-products and deletion peptides are formed in the synthesis.

The deprotection with TFA-CH$_2$Cl$_2$ is preferably conducted in the presence of small quantities of indole, e.g. about 0.01 to 0.1%, by weight, based on the total weight of TFA and CH$_2$Cl$_2$. The indole functions as a scavenger for potentially harmful oxidants, such as aldehydes, which may be present in TFA as an impurity. The deprotection temperature can range from about 0° C. to about 50° C., although room temperature, e.g. about 18° C. to 25° C., is preferred, and 25° C. is especially preferred. The deprotection reaction at 25° C. is generally completed within about 10 to 60 minutes, and usually 30 minutes is sufficient. Chloroform (CHCl$_3$) can be used in place of CH$_2$Cl$_2$.

After removal of the N$^\alpha$-Moz protecting group the acidolytic TFA deprotection step and prior to the next coupling step, the deprotected peptide-resin is neutralized. This neutralization is usually by exposure of the peptide-resin salt to an excess (e.g. 2.5% to 10% v/v) of a tertiary amine in a solvent, such as CH$_2$Cl$_2$, CHCl$_3$, or DMF. As the tertiary amine, triethylamine (Et$_3$N) is most commonly used. However, in accordance with a preferred embodiment of the invention, tributylamine (Bu$_3$N) is used as the tertiary amine neutralizing agent in place of Et$_3$N, particularly with CH$_2$Cl$_2$ or CHCl$_3$, and especially preferably CH$_2$Cl$_2$ as the solvent.

Thus, whereas TFA and Et$_3$N have relatively close boiling points, 72.4° C. and 89°–90° C., respectively, Bu$_3$N boils at 216°–217° C. Therefore, recovery of the CH$_2$Cl$_2$ or CHCl$_3$ solvent from the waste liquor (primarily methylene chloride (CH$_2$Cl$_2$), (bp=41° C.) or chloroform (CHCl$_3$, bp=61.2° C.) with lesser amounts of TFA, isopropyl alcohol, acids, bases, excess reagents and amino acids (minor)) by distillation will be greatly facilitated since the Bu$_3$N will not contaminate the distillate, thereby making it possible to recycle the bulk of CH$_2$Cl$_2$ or CHCl$_3$.

Steps (d), (e) and (f). Repetitive coupling/deprotecting

The preferred protected form of the fully protected resin bound thymosin el is shown by the following formula:

Ac-Ser(Bzl)-Asp(OBzl)-Ala-Ala-Val-Asp(OBzl)-Thr-(Bzl)-Ser(Bzl)-Ser(Bzl)-Glu(OBzl)-Ile-Thr-(Bzl)-Thr-(Bzl)-Lys(ClZ)-Asp(OBzl)-Leu-Lys(ClZ)-Glu(OBzl)-Lys(ClZ)-Lys(ClZ)Glu(OBzl)-Val-Val-Glu(OBzl)-Glu(OBzl)-AlaGlu(OBzl)-Asp(NH-CH(C$_6$H$_4$-CH$_3$)C$_6$H$_4$-resin)-OBzl where the protecting groups Bzl, OBzl and ClZ stand for benzyl, benzyl ester and 2-chlorobenzyloxycarbonyl, respectively, and Ac represents acetyl.

While specific protecting groups have been employed in describing the preferred embodiment for synthesis of thymosin $\alpha_1$, it is within the skill of the art to utilize equivalent conventional side-chain protecting groups. A side-chain protecting group should (1) be stable and render the side-chain functional group inert under the conditions employed in the coupling reaction, (2) be stable under the conditions employed in removing the $\alpha$-amino protecting group and (3) be readily removable upon completion of the desired amino acid sequence under reaction conditions that will not alter the structure of the peptide chain, or racemization of any of the chiral centers contained therein.

Details of suitable side-chain protecting groups for the amino acids can be found for example, in *Protective Groups in Organic Chemistry*, M. McOmie, Editor, Plenum Press, New York, 1973; and the aforementioned *The Peptides, Analysis, Synthesis, Biology*, Ed. by E. Gross and J. Meienhofer, Vol. 2, and Vol. 3.

The coupling of successive protected amino acids can be carried out in an automatic polypeptide synthesizer, as well known in the art. Each protected amino acid is preferably introduced in approximately 2.5 to 3.0 or more molar excess and the coupling may be carried out in dichloromethane, dichloromethane/DMF mixtures, DMF and the like, especially in methylene chloride at about ambient temperature. Other solvents which are known to be useful for the purpose of peptide-forming condensation reaction, for example, dimethylsulfoxide, pyridine, chloroform, dioxane, tetrahydrofuran, ethyl acetate, N-methylpyrrolidone, etc., as well as suitable mixtures thereof may also be used.

The reaction temperature for the condensation/coupling reaction may be selected from the range known to be useful for the purpose of peptide-forming condensation reactions. Thus, it may normally be within the range of about –40° C. to about 60° C., and preferably, about –20° C. to about 30° C. The coupling agent is normally DCC in dichloromethane but may be N,N'-di-iso-propylcarbodiimide or other carbodiimide either alone or in the presence of HBT, or N-hydroxysuccinimide. Alternatively, protected amino acid active esters (e.g. p-nitrophenyl, pentafluorophenyl and the like) or symmetrical anhydrides may be used.

After each successive coupling reaction the N$^\alpha$-Moz group is deprotected as described in step (c).

Step (g). Cleavage/deprotection

After the N-terminal residue, which in the case of thymosin $\alpha_1$ is acetylated, is coupled to the resin-bound peptide, the protected peptide is cleaved from the resin support. In the preferred embodiment cleavage of the protected peptide from the support and deprotection of the protected side-chain functional groups, are performed simultaneously by appropriate selection of the cleavage and deprotection reaction. When methylbenzhydrylamine resin is used as the support hydrogen bromide or trifluoromethane sulfonic acid is preferably used as the cleavage and deprotection agent. If benzhydrylamine resin is used then hydrogen fluoride is used. The cleavage/deprotection can be carried out as follows.

The protected thymosin $\alpha_1$ resin is suspended in trifluoroacetic acid and treated with dry hydrogen bromide gas at ordinary temperature (20°–25° C.) for about one hour in order to cleave the polypeptide from the resin and at the same time remove all the protecting groups from the side chains of the amino acid residues. Although hydrogen bromide may be used alone it is preferred to include anisole and, most preferably, a mixture of anisole and thioanisole in the trifluoroacetic acid when treating with dry hydrogen bromide gas. As previously described in Ser. No. 849,835 when a mixture of HBr, TFA and anisole is used as the deprotection and cleaving mixture, the yield of thymosin $\alpha_1$ is increased by about 50% over the instance when a mixture of only TFA and HBr is used. When a mixture of HBr, TFA, anisole and thioanisole is used, the yield is improved by about 90%. The volume ratio of anisole: thioanisole is preferably from about 20:80 to about 80:20, most preferably about 50:50 (i.e. about 1:1).

In an alternative embodiment trifluoromethane sulfonic 2 acid, CF$_3$.SO$_3$H, is used, instead of HBr as the cleavage/deprotection agent, again, preferably with anisole and especially preferably with anisole and thioanisole, in TFA. Unlike HBr gas, which is slowly bubbled through the suspension of the resin bound protected peptide in TFA, trifluoromethane sulfonic acid, being a liquid, can be added slowly, e,g, dropwise, or rapidly, all at once, generally at ordinary temperature, and like HBr, does not require any special laboratory apparatus for handling. The volume ratios of anisole and thioanisole as described above for the HBr, TFA, anisole and thioanisole mixture equally apply to the trifluoromethane sulfonic acid, TFA, anisole and thioanisole mixture.

The excess acids are then evaporated off at 40° C. under partial vacuum and the anisole and thioanisole are washed off with ether. Crude thymosin $\alpha_1$ is extracted from the residue with ammonium acetate (e.g. 1–2%) and desalted, for example, on a SEPHADEX G-10 column using 0.1N acetate acid as the eluent. Thereafter, the thymosin $\alpha_1$ may be purified by high pressure liquid chromatography (C$_{18}$ reversed phase column, 5.7×30 cm). When subjected to analytical high pressure liquid chromatography, the so obtained thymosin $\alpha_1$ behaves identically to reference thymosin $\alpha_1$ prepared by the fragment condensation method. Moreover, the presently synthesized thymosin $\alpha_1$ has been found indistinguishable from natural thymosin $\alpha_1$ and gives satisfactory amino acid analysis.

While the coupling and deprotection/cleavage reactions are typically carried out at about 25° C., higher or lower temperatures, for example, −10° C. to +50° C., are also suitable. The exact temperature for any particular reaction will, of course, be dependent upon the substrates, reagents, solvents and so forth, all being well within the skill of the practitioner.

Furthermore, although one specific sequence of purification steps of the deprotected thymosin $\alpha_1$ peptide was described above other procedures may also be used. Generally, the fully deprotected polypeptide may be purified by a sequence of chromatographic steps employing any or all of the following types: ion exchange chromatography on a weakly basic DEAE-SEPHADEX A-25 in the acetate form; gel permeation chromatography, e.g. on SEPHADEX G-25, hydrophobic adsorption chromatography on underivatized polystyrene-divinylbenzene (for example, AMBERLITE XAD); silica gel adsorption chromatography; or countercurrent distribution; high performance liquid chromatography (HPLC), especially reverse phase HPLC on octyl- or octadecylsilyl-silica bonded phase column packing.

Although the above description has been given with particular emphasis for the solid-phase peptide synthesis of thymosin $\alpha_1$, with its specified amino acid sequence and specified protected side-chain groups, the practitioner will readily recognize that the invention process can also be applied to fragments—shorter amino acid sequences—of the full 28 amino acid sequence of thymosin $\alpha_1$, including amino acid sequences beginning at the N-terminal serine-acetic acid and ending short of the C-terminal asparagine, or vice versa. Also, it is within the skill of the art to replace one or several of the amino acid residues of thymosin $\alpha_1$ with other amino acid residues to achieve specific properties while retaining the essential biochemical characteristics of thymosin $\alpha_1$. Likewise, it is within the skill of the art to add one or more, such as up to about 10, preferably up to about 6, amino acid residues at either or both of the N- and C-terminals to obtain peptides of up to about 48, preferably up to about 40 amino acids, and comprising therein the thymosin $\alpha_1$ peptide.

However, the most notable benefits flowing from the use of the $N^\alpha$-Moz protection will generally be observed for the longer peptide sequences of at least about 20 amino acids, since the cumulative effects of the milder acidolytic deprotection of the $N^\alpha$-Moz group and the volume savings of the acid solvent (TFA) become more pronounced as the number of coupling/deprotection cycles increase.

Where thymosin $\alpha_1$ fragments or analogs are prepared with C-terminal amino acids which do not have the amide group (—$CONH_2$), conventional solid supports rather than the preferred methylbenzhydrylamine resin or benzhydrylamine resin will be used.

Suitable solid supports useful for the solid-phase peptide synthesis are those materials which are inert to the reagents and reaction conditions of the stepwise condensation-deprotection reactions, as well as being insoluble in the media used. Suitable solid supports are chloromethyl-polystyrene-divinylbenzene polymer, hydroxymethyl-polystyrene-divinylbenzene polymer, functionalized, crosslinked poly-N-acrylylpyrrolidine resins, and the like, especially chloromethylpolystyrene-1% (or 2%) divinylbenzene polymer. The attachment to the chloromethyl polystyrene-divinylbenzene type of resin is made by means of the reaction of the Moz-amino acid, as its cesium, tetramethylammonium, triethylammonium, 4,5-diazabicyclo-[5.4.0]undec-5-ene, or similar salt in ethanol, acetonitrile, N,N-dimethylformamide (DMF), and the like, especially the cesium salt in DMF, with the chloromethyl resin at an elevated temperature, for example, between about 40° and 60° C., preferably about 50° C., for from about 12 to 48 hours, preferably about 24 hours.

This invention is further illustrated by the following non-limiting examples.

REFERENTIAL EXAMPLE 1

Methylbenzhydrylamine Resin 50.9 gm of polystyrene resin beads (copolystyrene-1%-divinylbenzene, 200–400 mesh beads, from Lab Systems, San Mateo, Calif.) were suspended in 500 ml of dichloroethane. The mixtures were cooled in an ice-bath with gentle mechanical stirring until the temperature went below 5° C.

15.5 g of p-toluoyl chloride and 13.3 g of aluminum chloride were mixed in 250 ml of dichloroethane in a dropping funnel. The solution was added dropwise to the cooled, stirred suspension of the resin beads over a period of about 40 minutes, care being taken not to allow the reaction to warm up above 5° C. The stirring was continued for 4 hours at room temperature when the resin was washed sequentially with isopropanol, isopropanol-water (1:1 mixture), isopropanol and dried to give 53.8 of p-toluoyl resin. This resin was then mixed with 168 g of ammonium formate, 201 ml of formamide, 134 ml of formic acid and 350 ml of nitrobenzene, The mixture was gradually heated up to 165°–168° C. under reflux and maintained for 1 day during which time about 115 ml of the aqueous phase was collected from a Dean-Stark trap. The resin was washed and dried as above to yield 55.5 g of N-formyl methylbenzhydrylamine resin. The product was hydrolyzed in a mixture of 300 ml each of 12N HCl and isopropanol under reflux for 3 hours. Washing and drying the resulting resin provided 54.9 g of the hydrochloride form of methylbenzhydrylamine resin. It showed a very strong positive reaction to ninhydrin reagent and incorporated 0.4 mmol of Moz-Ala-OH when neutralized and coupled with Moz-Ala-OH in the presence of dicyclohexylcarbodiimide.

REFERENTIAL EXAMPLE 2

Synthesis of Leu-Ala-Gly-Val

Moz-Val-$OCH_2$—$C_6H_4$-Resin (1.0 g; 0.52 mmol/g) was placed in the reaction cup of a BECKMAN 990B automatic peptide Synthesizer and the synthesis carried out with Moz-Gly-OH (0.5 g) in the first cycle, Moz-Ala-OH (0.53 g) in the second cycle, and Moz-Leu-OH (0.62 g) in the last cycle utilizing the DCC (0.43 g) coupling procedure. The instrument was programmed to perform the following steps in each cycle: 1) prewash with 20 volumes of 10% TFA in $CH_2Cl_2$ containing 0.05% indole, 2) stir in 10% TFA for 28 minutes, 3) wash 3 times with $CH_2Cl_2$, 4) prewash with 10% triethylamine ($Et_3N$) in $CH_2Cl_2$, 5) stir in 10% $Et_3N$ for 5 minutes, 6) wash 3 times with $CH_2Cl_2$, 7) add Moz-amino acid and DCC, then stir for 120 minutes, 8) 3 washings each with (a) $CH_2Cl_2$, (b) isopropyl alcohol (i-PrOH):$CH_2Cl_2$ mixture (1:1) and (c) $CH_2Cl_2$. No double coupling was used for the entire synthesis. The completed tetrapeptide-resin Moz-Leu-Ala-Gly-Val-$OCH_2$—$C_6H_4$-Resin (1.15 g) was treated with HF (10 ml) in the presence of anisole (1 ml) at 0° for 45 minutes. Removal of the excess acid and anisole in vacuo and extraction with water yielded 0.22 g of crude Leu-Ala-Gly-Val. It had an amino acid composition of Gly, 0.95; Ala, 1.03; Val, 1.01; Leu, 1.00. Analytical HPLC on BECKMAN ALTEX MODEL 344 GRADIENT SYSTEM using a HAMILTON PRP-1 reverse phase column (4.1×150 mm), eluted with linear gradients of pH 6.0, 0.03M potassium phosphate, 4–12.5% acetonitrile, indicated that the material was about 98% pure. It was analyzed on a BECKMAN MODEL 120B AMINO ACID ANALYZER to determine the content of deletion peptides by ion-exchange chromatography, and the results are listed in Table I.

A parallel synthesis of the same compound was carried out under identical conditions except Boc-Val-OCH$_2$—C$_6$H$_4$-Resin and Boc-amino acids (from Peptide Institute, Inc., Osaka, Japan) were used in place of Moz-derivatives. The resultant Boc-Leu-Ala-Gly-Val-OCH$_2$—C$_6$H$_4$-Resin (1.10 g) was treated with HF-anisole and worked up as above to yield 0.20 g of crude Leu-Ala-Gly-Val, which showed an HPLC pattern almost identical with that obtained from the Moz-experiment. Amino acid analysis: Gly, 0.97; Ala, 1.00; Val, 1.00;; Leu, 0.97. The results of the deletion peptide analysis, on an amino acid analyzer, are also shown in Table I.

REFERENTIAL EXAMPLE 3

Rates of Cleavage of Moz-group and Boc-group by TFA

Moz-Ala-Leu-Leu-Leu-Leu-Leu-Val-OCH$_2$—C$_6$H$_4$-Resin (0.5 g, 0.42 mmol/g) which was prepared following the same procedure used in Referential Example 2 was stirred with 20 volumes of 5% TFA in CH$_2$Cl$_2$. At desired time intervals, samples (20% of total each) were withdrawn, immediately placed on a sintered glass filter, suction dried, quenched with 10% Et$_3$N in CH$_2$Cl$_2$ and washed thoroughly with more CH$_2$Cl$_2$. The neutralized peptide-resin samples (ninhydrin positive) were transferred into small capped vials and each stirred with Boc-Phe-OH (53 mg) and DCC (41.2 mg) in 1 ml of CH$_2$Cl$_2$ for 2 hours. The peptide-resins became ninhydrin negative. After thorough washing with CH$_2$Cl$_2$, i-PrOH—CH$_2$Cl$_2$ (1:1), and MeOH, followed by drying the samples were individually hydrolyzed in dioxane-HCl (1:1) at 110° for 24 hours and then analyzed for their amino acid compositions. The ratio Phe/Ala was taken as the fraction of protecting group removed before the final coupling. The same experiments were repeated with 10% TFA on Moz-Ala-Leu-Leu-Leu-Leu-Leu-Val-OCH$_2$—C$_6$H$_4$-Resin and also with 40%, 20%, 20% and 5% TFA on Boc-Ala-Leu-Leu-Leu-Leu-Leu-Val-OCH$_2$—C$_6$H$_4$-Resin. The results are shown in FIG. 1.

Example 1

Synthesis of Thymosin $\alpha_1$

MBHA-resin (1.00 g; 0.40 mmol/g) as obtained in Referential Example 1 was placed inside the reaction cup of a Beckman 990B automatic synthesizer and neutralized with 10% Et$_3$N (20 vol, 10 minutes), washed 3 times with CH$_2$Cl$_2$ and then coupled with three-fold excess of Moz-aspartic acid $\alpha$-benzyl ester (equivalent amount of DCC, 2 hours). The automatic synthesis was continued by adding the appropriate Moz-amino acid in each cycle similar to that programmed for the model tetrapeptide synthesis described above in Referential Example 2. Three-fold excesses of Moz-amino acid and DCC were used in each cycle. For deprotection of the Moz-group, 10% TFA in CH$_2$Cl$_2$ with 0.05% indole (30 minutes) was utilized. The protected thymosin $\alpha_1$-Resin Ac-Ser(Bzl)-Asp(OBzl)-Ala-Ala-Val-Asp(Bzl)-Thr(Bzl)-Ser(Bzl)-Ser(Bzl)-Glu(OBzl)-Ile-Thr-(Bzl)-Thr(Bzl)-Lys(ClZ)-Asp(OBzl)-Leu-Lys(ClZ)-Glu-(OBzl)-Lys(ClZ)-Lys(ClZ)-Glu(OBzl)-Val-Val-Glu(OBzl)-Glu(OBzl)-Ala-Glu(OBzl)-Asp(MBHA-Resin)-OBzl thus obtained weighed 3.55 g.

Figure 2:
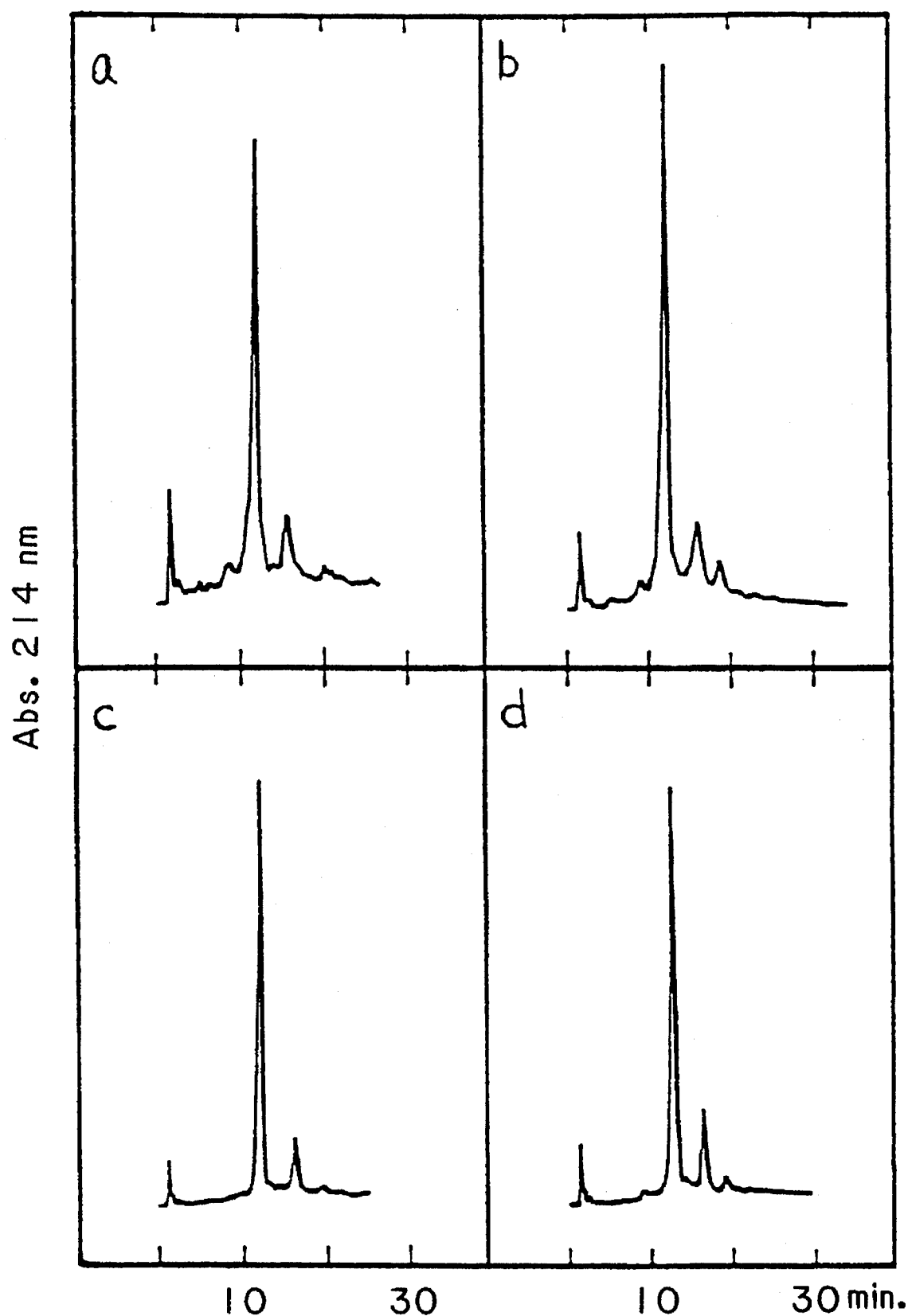
FIG. 2 shows a chromatographic tracings of the HPLC analysis for the crude thymosin α$_1$ produced by (a) Boc protection with HF cleavage, (b) Boc protection with HBr cleavage, (c) Moz protection with HF cleavage and (d) Moz protection with HBr cleavage.
Figure 3:
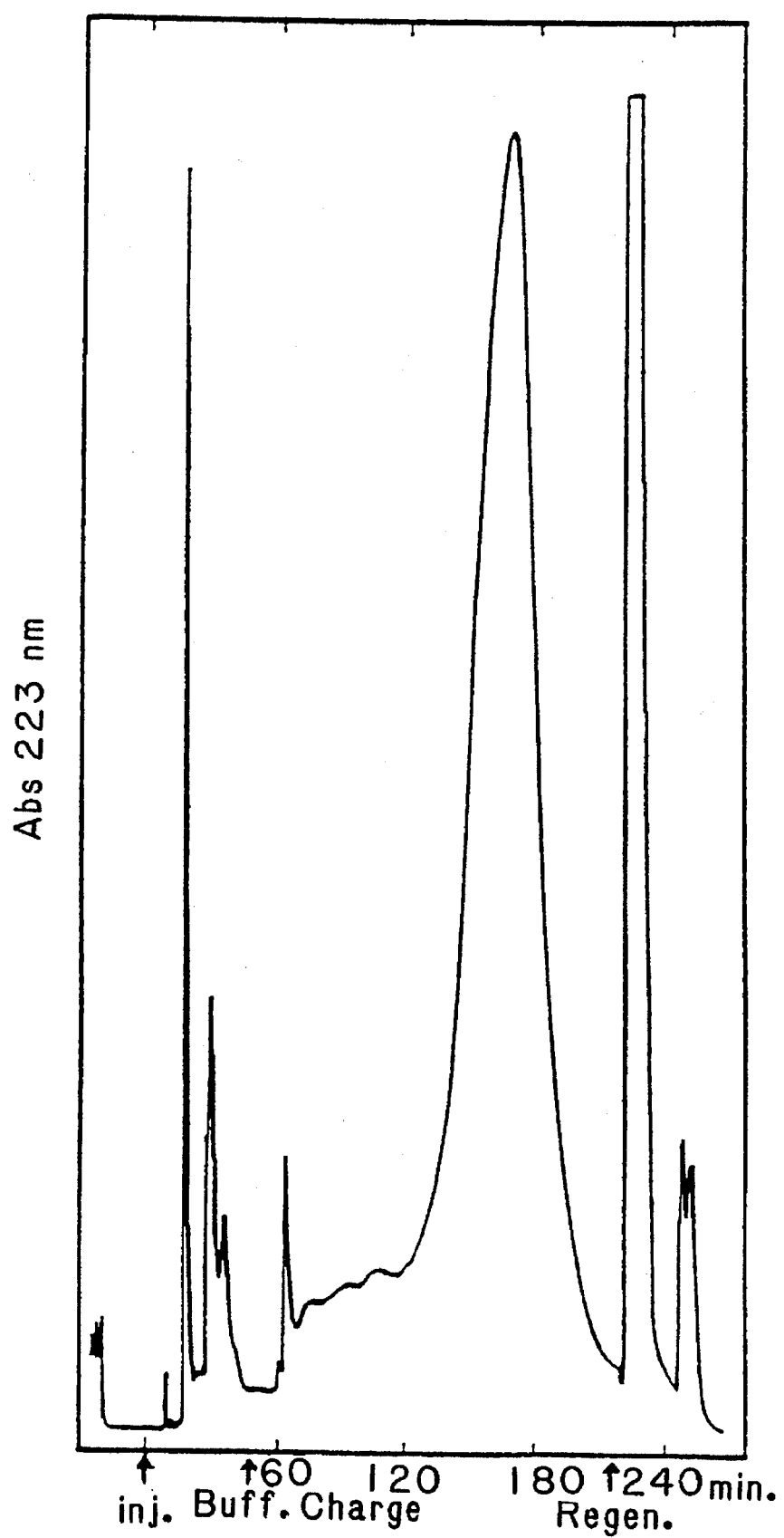
FIG. 3 is a chromatographic tracing of the preparative HPLC purification of thymosin α$_1$ under the conditions described in Example 1.
Figure 4:
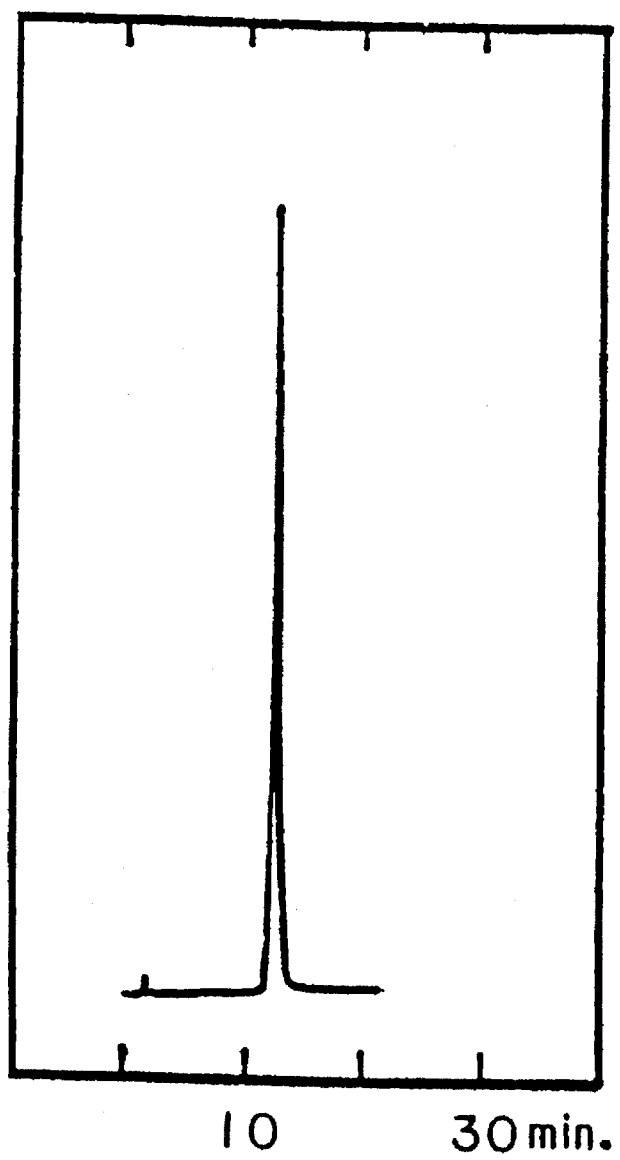
FIG. 4 is a chromatographic tracing of an analytical HPLC for purified thymosin α$_1$ as obtained in Example 1; and, FIGS. 5a–b show chromatographic tracings of an analytical HPLC for (FIG. 5a) crude and (FIG. 5b) purified thymosin α$_1$ as obtained in Example 2.

Part of this protected peptide-resin (1.05 g) was suspended in a mixture of TFA (16 ml), anisole (2 ml) and thioanisole (2.2 ml) in ordinary laboratory glassware and a steady stream of dry HBr gas was bubbled through for 60 minutes. The excess acids were quickly evaporated off on a rotary evaporator (38° C., 5 minutes) and the residue washed onto a sintered glass filter with dry ether. After further washing with more ether, the peptide was extracted into two portions of 25 ml of 2% ammonium acetate. The solution was concentrated to a smaller volume, desalted on a SEPHADEX G-10 column (2.6×95 cm; 0.1M HOAc) and lyophilized to give 0.351 g of crude thymosin $\alpha_1$. Analytical HPLC of this material is shown in panel (d) of FIG. 2. The crude product was purified on the preparative HPLC (eluted with pH 5.0, 0.3M potassium phosphate, stepped gradient 9% to 10.37% CH$_3$CN) (FIG. 3) followed by desalting on a SEPHADEX G-10 column (5.2×95 cm; 0.1M HOAc) to provide 0.123 g (35% yield) of thymosin $\alpha_1$ (see FIG. 4) which migrated identically with the natural hormone and the standards prepared elsewhere in analytical HPLC. *Amino Acid Analysis* (24 hour hydrolysis): Asp, 3.95; Thr, 2.89; Ser, 2.69; Glu, 6.20; Ala, 2.90; Val, 2.44; Ile, 0.95; Leu, 1.00; Lys, 4.01, (100 hour hydrolysis): Asp, 4.09; Thr, 2.74; Ser, 2.13; Glu, 6.26; Ala, 2.92; Val, 3.00; Ile, 0.95; Leu, 1.00; Lys 4.13.

Another portion of this protected peptide-resin (0.55 g) was mixed with 1 ml anisole and stirred with 10 ml HF at 0° C. for 45 minutes in an HF-apparatus as described in Stewart, J. M. & Young, J. D. (1984) *Solid Phase Peptide Synthesis,* 2nd Ed., Pierce Chemical Company, Rockford, Ill.; and Sakakibara, S., Kishida, Y., Kikuchi, Y., Sakai, R. and Kakiuchi, K. (1968) *Bull. Chem. Soc. Japn.,* 41, 1273–1276. The volatile components were evaporated off, first with water aspirator, then with high vacuum pump, and the residue washed onto a sintered glass filter with ether. Work up as above yielded 0.189 g of crude product which showed a chromatographic pattern similar to that of the material above (see panel (c) of FIG. 2).

A parallel synthesis of thymosin $\alpha_1$ using Boc-amino acids in place of Moz-amino acids was carried out in the same manner in the automatic synthesizer employing the identical program, except that 40% TFA in CH$_2$Cl$_2$ containing 0.05% indole (30 minutes) was used as the deprotecting reagent. From 1.05 g of the same MBHA-Resin, 3.36 g of protected thymosin $\alpha_1$-Resin was obtained. Cleavage of 1.01 g of this peptide-resin by the HBr procedure as described above afforded 0.325 g of crude thymosin $\alpha_1$. The analytical HPLC pattern is shown in panel (b) of FIG. 2. After preparative HPLC purification and desalting 0.095 g (29% yield) of pure material was obtained. *Amino Acid Analysis* 24 hour hydrolysis: Asp, 4.01; Thr, 2.93; Ser, 2.44; Glu, 6.15; Ala, 3.00; Val, 2.37; Ile, 0.86; Leu, 1.00; Lys, 4.14.

The same protected peptide resin from the Boc-method was also cleaved by the HF procedure. From 0.5 g of the resin, 0.166 g of crude peptide was obtained. The analytical HPLC pattern is shown in panel (a) of FIG. 2.

In these examples, a WATERS PREPLC/SYSTEM 500A with PRE-PACK-500/C$_{18}$ column (5×30 cm) was used for the preparative HPLC purification of the synthetic peptides. Commerically available HPLC grade solvents and reagent grade chemicals were used without further purification.

For amino acid analyses, a BECKMAN MODEL 6300 HIGH PERFORMANCE ANALYZER was used.

Example 2

This example demonstrates the use of trifluoromethane sulfonic acid for deprotection and cleavage of thymosin $\alpha_1$-Resin.

Protected thymosin $\alpha_1$-Resin (0.508 g) that was prepared from MBHA-Resin with Moz-amino acids on the automatic peptide synthesizer (BECKMAN 990B) as described in Example 1, was mixed with 1 ml of anisole, 1 ml of thioanisole, 3 ml of trifluoroacetic acid and treated with 0.3 ml of trifluoromethane sulfonic acid added dropwise during 1 minute period of time while being stirred gently with a magnetic bar. After 60 minutes more of stirring, the mixture was poured into 100 ml of dry ether. The gummy precipitate that formed was washed briefly a few more times with fresh ether and the peptide extracted with 30 ml of 2% ammonium acetate followed by a few ml of water. The combined extracts were then filtered to remove the solid matters, concentrated to a smaller volume and desalted on a SEPHADEX G-10 column (2.6×85 cm, 0.1M HOAc). Lyophilization of the peptide peak provided 0.164 g of crude thymosin $\alpha_1$. FIG. 5-a shows the analytical HPLC of the crude thymosin $\alpha_1$.

The crude peptide was then purified on a HAMILTON PRP-1 column (21.5×250 mm, 10 micron, pH 6, 6.5% acetonitrile) to give 0.057 g of purified thymosin $\alpha_1$. Analytical HPLC of this material is shown in FIG. 5-b.

Amino acid analysis: (6N HCl, 100°)

24 hour hydrol. Asp, 4.00; Thr, 2.91; Ser, 2.80; Glu, 5.99; Ala, 2.87, Val, 2.13; Ile, 0.96; Leu, 1.01; Lys, 3.83.

100 hour hydrol. Asp, 4.00; Thr, 2.79; Ser, 2.30; Glu, 5.90; Ala, 2.85; Val, 2.66; Ile, 0.96; Leu, 1.09; Lys, 3.93.

As a result of the use of Moz as the $N^\alpha$ protecting group in the solid phase peptide synthesis according to this invention, not only are higher yields and higher purities of the object thymosin el achieved, but also there is the additionally important advantage of consuming only about 20% to about 25% of the total volume of TFA as compared with about the same yield of peptide using the Boc protecting group. Disposal of the liquid waste will, therefore, be easier and the amount of pollutant escaping into the environment will be greatly reduced.

Using trifluoromethane sulfonic acid in place of HBr or HF as the cleavage/deprotection agent provides similar advantages to HBr but in addition avoids the use of pressurized HBr gas and the inconvenience of having to bubble the gas through the suspended peptide-resin.

Still further improvements in the overall yield are obtained when thioanisole and anisole are simultaneously used during cleavage/deprotection.

The efficiency of the overall process is further enhanced by using tributylamine as the neutralizing agent, thereby permitting recycling of the methylene chloride, chloroform or other relatively low boiling solvent.

Although the foregoing invention has been described in some detail by way of illustration and example for purposes of clarity of understanding, it will be obvious that certain changes and modifications may be practiced within the scope of the appended claims.

What is claimed:

1. The process for producing thymosin $\alpha_1$, or a biologically active analog or fragment thereof by solid-phase peptide synthesis, comprising the steps of (a) temporarily chemically protecting the reactive amino group at the alpha-position, and any other reactive groups, other than beta carboxylic acid group, on the C-terminal amino acid of the thymosin $\alpha_1$ peptide with 4-methoxybenzyloxycarbonyl; (b) chemically bonding the protected C-terminal amino acid via the unprotected carboxylic acid (—COOH) group thereof to a resin support; (c) chemically deprotecting the reactive amino group of the resin-bound protected amino acid by acidolytic cleavage using liquid trifluoroacetic acid; (d) chemically coupling via a peptide bond the next amino acid in the desired sequence by contacting the resin-bound amino acid from step (c) with the next amino acid in the desired sequence with all of the reactive groups thereof, other than the carboxylic acid group at the alpha-position, chemically protected with 4-methoxybenzyloxycarbonyl, in the presence of a coupling agent; (e) chemically deprotecting the reactive amino group of the coupled amino acid from step (d) by acidolytic cleavage using liquid trifluoroacetic acid; (f) continuing the synthesis by repeating steps (d) and (e) with successive amino acids in the desired sequence being added one at a time until the total desired sequence of the protected peptide is built up on the resin; and (g) cleaving the protected peptide from the resin support and deprotecting protected reaction groups using liquid trifluoroacetic acid, whereby the volume of liquid trifluoroacetic acid used in steps (c) and (e) is substantially reduced as compared to the volume of liquid trifluoroacetic acid required in steps (c) and (e) when the alpha-amino groups of each successive amino acid are protected with tert-butyloxycarbonyl (BOC); said process further comprising neutralizing the chemically deprotected resin-bound amino acid from steps (c) and (e) with tributylamine.

* * * * *